(12) United States Patent
Grass et al.

(10) Patent No.: US 8,907,129 B2
(45) Date of Patent: Dec. 9, 2014

(54) PROCESS FOR PREPARING DECANECARBOXYLIC ACIDS

(75) Inventors: Michael Grass, Haltern am See (DE); Alfred Kaizik, Marl (DE); Hans-Gerd Lueken, Marl (DE); Wilfried Bueschken, Haltern am See (DE)

(73) Assignee: EVONIK DEGUSSA GmbH, Essen (DE)

( * ) Notice: Subject to any disclaimer, the term of this patent is extended or adjusted under 35 U.S.C. 154(b) by 363 days.

(21) Appl. No.: 13/386,523

(22) PCT Filed: May 25, 2010

(86) PCT No.: PCT/EP2010/057157
§ 371 (c)(1),
(2), (4) Date: Mar. 26, 2012

(87) PCT Pub. No.: WO2011/009657
PCT Pub. Date: Jan. 27, 2011

(65) Prior Publication Data
US 2012/0172624 A1    Jul. 5, 2012

(51) Int. Cl.
*C07C 51/235*    (2006.01)
*C07C 45/74*    (2006.01)
*C07C 45/62*    (2006.01)
*C07C 45/50*    (2006.01)

(52) U.S. Cl.
CPC ............. *C07C 45/74* (2013.01); *C07C 45/50* (2013.01); *C07C 45/62* (2013.01); *C07C 51/235* (2013.01)
USPC ..................................... 562/512.2

(58) Field of Classification Search
CPC ........ C07C 51/235; C07C 45/74; C07C 45/62
USPC ..................................... 562/512.2
See application file for complete search history.

(56) References Cited

U.S. PATENT DOCUMENTS

| 7,381,838 B2 | 6/2008 | Wiese et al. |
| 8,461,394 B2 * | 6/2013 | Lueken et al. ................ 568/454 |
| 2006/0052633 A1 | 3/2006 | Lee et al. |
| 2011/0130595 A1 | 6/2011 | Lueken et al. |
| 2012/0035382 A1 | 2/2012 | Priske et al. |

FOREIGN PATENT DOCUMENTS

| DE | 102 25 282 | 12/2003 |
| DE | 10 2008 002 187 | 12/2009 |
| EP | 0 439 013 | 7/1991 |
| FR | 2 769 624 | 4/1999 |
| WO | 01 46111 | 6/2001 |
| WO | 2004 108648 | 12/2004 |
| WO | 2011 045102 | 4/2011 |

OTHER PUBLICATIONS

International Search Report Issued Feb. 4, 2011 in PCT/EP10/57157 Filed May 25, 2010.
U.S. Appl. No. 13/256,116, filed Sep. 12, 2011, Kaizik, et al.
U.S. Appl. No. 13/498,690, filed Mar. 28, 2012, Kaizik, et al.

* cited by examiner

*Primary Examiner* — Yong Chu
(74) *Attorney, Agent, or Firm* — Oblon, Spivak, McClelland, Maier & Neustadt, L.L.P.

(57) ABSTRACT

The invention relates to a process for preparing a mixture of isomeric decane-carboxylic acids, which comprises the following steps:
a) hydroformylation of a hydrocarbon mixture containing linear C4-olefins using a rhodium-containing catalyst system;
b) aldol condensation of a mixture of aliphatic C5-aldehydes obtained from step a);
c) selective hydrogenation of the mixture of unsaturated C10-aldehydes from step b) to aliphatic C10-aldehydes;
d) uncatalysed oxidation of the mixture of aliphatic C10-aldehydes from step c) to give a mixture having a proportion of at least 70% by mass of 2-propylheptanoic acid, based on the total content of isomeric decanecarboxylic acids.

11 Claims, No Drawings

PROCESS FOR PREPARING DECANECARBOXYLIC ACIDS

This application is a National Stage of PCT/EP10/057157 filed May 25, 2010 and claims the benefit of DE 10 2009 027 978.4 filed Jul. 23, 2009.

The present invention relates to the preparation of decanecarboxylic acids, in particular decanecarboxylic acid mixtures having a high proportion of 2-propylheptanoic acid.

Decanecarboxylic acids can be used, for example, as intermediate for the preparation of peresters, detergents and lubricants.

The preparation of pentanal mixtures by hydroformylation of a mixture of linear butenes is described in the patent texts DE 101 08 474, DE 101 08 475, DE 101 08 476 and DE 102 25 282. In all the patent texts, a rhodium catalyst having a diphosphine ligand having a xanthene skeleton is used in at least one hydroformylation step. This catalyst enables 2-butenes to be hydroformylated under isomerizing conditions. The ratio of n-pentanal to 2-methylbutanal is 85:15. Documents DE 101 08 474 and DE 101 08 475 discloses processes in which the hydroformylation is carried out in two stages. In the first hydroformylation stage, 1-butene is converted in a selectivity of 95% into n-pentanal using a catalyst comprising rhodium and a monophosphine as ligand. The unreacted butenes, mainly 2-butenes, are reacted in the second hydroformylation stage using the abovementioned rhodium/bisphosphine. Documents DE 101 08 476 and DE 102 25 282 claim single-stage hydroformylation processes. As use for the n-pentanal/2-methylbutanal mixture, all four patent texts claim, inter alia, the preparation of a mixture of isomeric decanecarboxylic acids. A synthetic route comprising the following steps is outlined: aldol condensation of the pentanal mixture to form a decenal mixture, selective hydrogenation of the decenal mixture to form a decanal mixture and oxidation of the latter to give a mixture of isomeric decanecarboxylic acids. Neither the ability to carry out this synthesis nor an embodiment are demonstrated. It is merely stated that it could be carried out by a method analogous to the preparation of 2-ethylhexanoic acid from butyraldehyde, with, in particular, the following two literature references being cited. The first reference is Ullmann's Encyclopaedia of Industrial Chemistry, 5th Edition, Volume A1, p. 330. Here, it is described in one sentence how 2-ethylhexenal can be hydrogenated to 2-ethylhexanal. No further reaction conditions are mentioned. There are also no references to the literature. The second reference is Ullmanns Encyclopädie der Technischen Chemie, 4th edition 1975, volume 9, page 144. Here, it is stated, without any details being given, that 2-ethylhexanoic acid can be prepared by oxidation of 2-ethylhexanal and that additions of alkali metal salts of 2-ethylhexanoic acid increase the yields. Literature references are likewise lacking. In DE 101 08 476, it is stated that the condensation mixture (decenal) can, depending on the reaction conditions selected, be hydrogenated either partially to decanals in the presence of palladium-containing catalysts or fully to form decanols. Descriptions of the catalyst and an indication of reaction conditions and the way of carrying out the reaction are lacking.

Thus, no process for preparing decanecarboxylic acids has been disclosed sufficiently completely for it to be able to be performed by a person skilled in the art without carrying out complicated experiments.

It was an object of the present invention to develop a process which provides decanals in a few steps from a hydrocarbon mixture containing linear C4-olefins and additionally isobutene which are oxidized by means of oxygen-containing gases in high yields to the corresponding decanecarboxylic acids without either a catalyst or stabilizing additives being used.

The invention accordingly provides a process for preparing a mixture of isomeric decanecarboxylic acids, which comprises the following steps:

a) hydroformylation of a hydrocarbon mixture containing linear C4-olefins using a rhodium-containing catalyst system;
b) aldol condensation of a mixture of aliphatic C5-aldehydes obtained from step a);
c) selective hydrogenation of the mixture of unsaturated C10-aldehydes from step b) to aliphatic C10-aldehydes;
d) uncatalysed oxidation of the mixture of aliphatic C10-aldehydes from step c) to give a mixture having a proportion of at least 70% by mass of 2-propylheptanoic acid, based on the total content of isomeric decanecarboxylic acids.

The process of the invention has the following advantages: the oxidation is very selective even at very high conversions, so that only small losses of material occur. Accordingly, only small amounts of by-products which have to be disposed are obtained. Since no catalyst is used, no costs are incurred for the catalyst, for separating off the used catalyst or products derived therefrom or for disposal of these.

In the present invention, the decanal mixture which has been prepared from linear butenes in a three-stage synthesis and contains, based on the decanals present, at least 80% by mass of 2-propylheptanal is oxidized to the corresponding decanecarboxylic acids. According to the invention, the oxidation is carried out neither with addition of a catalyst, usually a transition metal compound, nor with addition of a stabilizer, for example an alkali metal salt or alkaline earth metal salt of a carboxylic acid.

As oxidant, it is possible to use oxygen, air or other oxygen-containing gas mixtures. Preference is given to using oxygen or oxygen/nitrogen mixtures containing more than 10% by volume of oxygen in the process of the invention.

The oxidation is carried out in the temperature range from 10 to 80° C., in particular in the temperature range from 20 to 50° C., very particularly preferably in the temperature range from 25 to 35° C.

The absolute reaction pressure, measured in the gas phase at the top of the reactor, is from 0.1 to 1 MPa, in particular from 0.1 to 0.5 MPa.

The oxidation is carried out in the mixed liquid/gas phase. The decanal mixture and/or the decanecarboxylic acid mixture formed therefrom is present as a continuous liquid phase into which the oxidizing gas or gas mixture is passed. The major part of the gas mixture is present as disperse phase.

As reactors, it is possible to use stirred vessels or bubble column reactors into which gas is introduced in the vicinity of the bottom by means of a gas distribution device, for example a frit or nozzle.

To avoid the formation of an explosive mixture, nitrogen is introduced into the gas space above the surface of the liquid in such an amount that the content of oxygen in the gas space (offgas) does not exceed 6% by volume.

The oxidation can be carried out continuously or batchwise in one or more reactor(s). When a plurality of reactors is used, these can be connected in series and/or in parallel.

In a batchwise mode of operation, a conversion of the aldehydes of from 60 to 98%, in particular from 85 to 95%, is sought.

In continuous operation, a conversion of the aldehydes of from 50 to 95%, in particular from 70 to 90%, is sought.

After the oxidation, the reaction mixture comprises decanecarboxylic acids having a proportion of 2-propylheptanoic acid of at least 70% by mass, unreacted $C_{10}$-aldehydes, by-products and possibly materials which were originally present in the decanal used. The content of decanecarboxylic acids in this mixture is in the range from 50 to 98% by mass, in particular in the range from 80 to 93% by mass.

This mixture is preferably fractionated by distillation. The fractional distillation can be carried out at atmospheric pressure or under reduced pressure. The fractional distillation is preferably carried out under reduced pressure.

The oxidation mixture is preferably separated into the following four fractions:
 a) a low boiler fraction containing essentially degradation products formed in the oxidation
 b) an aldehyde fraction comprising mainly decanals
 c) a product fraction containing virtually only decanecarboxylic acids
 d) a high boiler fraction.

The fractional distillation is preferably carried out continuously or semicontinuously in three columns connected in series. The low boilers are separated off in the first column, the aldehydes are separated off in the second column and the decane-carboxylic acids are separated off in the third column, in each case as overhead product. The high boilers are obtained as bottom product from the third column.

The low boilers and high boilers which have been separated off can be utilized thermally or be used as starting material for a synthesis gas plant. If the high boiler fraction contains a large proportion of decanecarboxylic esters, it can optionally be worked up to obtain decanecarboxylic acids.

The aldehyde fraction separated off can be recirculated in its entirety or partly to the oxidation stage.

The decanecarboxylic acids obtained can be used, for example, for the preparation of peresters, desiccants, detergents, plasticizers or lubricants.

Starting materials for the process of the invention are hydrocarbon mixtures which have no multiply unsaturated compounds and no acetylene compounds and contain at least one of the olefins cis-2-butene, trans-2-butene and 1-butene. In addition, up to 5% by mass, in particular up to 1% by mass, very particularly preferably up to 0.2% by mass, of isobutene, in each case based on the $C_4$-olefin fraction, can be present in the starting materials.

Industrial mixtures containing linear $C_4$-olefins are light petroleum spirit fractions from refineries, $C_4$-fractions from FC crackers or stream crackers, mixtures from Fischer-Tropsch syntheses, mixtures from dehydrogenation of butanes, mixtures formed by metathesis or mixtures from other industrial processes.

For example, mixtures of linear butenes which are suitable for the process of the invention can be obtained from the $C_4$ fraction of a steam cracker. In this case, butadiene is removed in a first step. This is effected either by extraction or extractive distillation of the butadiene or selective hydrogenation of the latter. In both cases, a virtually butadiene-free $C_4$ fraction, viz. raffinate I, is obtained. In the second step, isobutene is removed from the $C_4$ stream, e.g. by preparation of methyl tert-butyl ether (MTBE) by reaction with methanol or preparation of ethyl tert-butyl ether by reaction with ethanol. Other possibilities are reaction of the isobutene in the raffinate I with water to form tert-butanol or acid-catalysed oligomerization of the isobutene to form diisobutene. The now isobutene-free $C_4$ fraction, viz. raffinate II, contains, as desired, the linear butenes and possibly butanes. Optionally, the 1-butene can also be separated off by distillation. Both fractions, those containing 1-butene or those containing 2-butene, can be used in the process of the invention.

A further possible way of preparing a suitable starting material is to hydroisomerize raffinate I, raffinate II or a hydrocarbon mixture having a similar composition in a reactive column. Here, it is possible to obtain, inter alia, a mixture comprising 2-butenes, small proportions of 1-butene and possibly n-butane and also isobutane and isobutene.

A further feed mixture for the process of the invention is the $C_4$ mixture remaining after the oligomerization of a mixture of linear olefins (for example raffinate II or raffinate III), which comprises butane, possibly isobutene, 2-butenes and small amounts of 1-butene.

Preference is given to using hydrocarbon mixtures having, preferably, at least 15% by mass of linear butenes.

The first step of the process of the invention is the hydroformylation. To obtain a proportion of 2-propylheptanoic acid of over 80% in the end product, it is necessary for n-pentanal to be formed in a selectivity of greater than 85% in the hydroformylation of linear butenes. If only 1-butene is to be reacted, the hydroformylation can, for example, be effected with the aid of a catalyst system comprising rhodium and a monophosphine, for example triphenylphosphine. If 2-butenes are also to be reacted, the hydroformylation has to be carried out under isomerizing conditions. This means that a catalyst which is, under the reaction conditions, able both to shift the double bonds in all linear butenes, i.e. isomerize them, and also to hydroformylate them terminally is used. Use is made of catalysts which convert linear butenes having any ratios of the isomers into pentanals with an n selectivity (ratio of n-pentanal to the sum of all $C_5$-aldehydes) of greater than 85%. As catalyst for this purpose, it is possible to use, for example, the bisphosphines described in the patent texts DE 101 08 474, DE 101 08 476, DE 101 08 476 and DE102 25 282. Rhodium catalysts having bulky aromatic bisphosphites as ligands, as described, for example, in EP 0 213 639, can likewise be used for this purpose.

The second reaction step of the process of the invention is the aldol condensation of the $C_5$-aldehydes to form decenals. The reaction product of the first stage comprises, after removal of the unreacted hydrocarbons, n-pentanal (valeraldehyde), 2-methylbutanal and small amounts of n-pentanol and 2-methylbutanol. If the hydrocarbon feed mixture contains isobutene, 3-methyl-butanal is present in the reaction mixture from the first stage. The aldehyde fraction contains at least 85% by mass of n-pentanal, less than 15% by mass of 2-methylbutanal and less than 5% by mass of 3-methylbutanal, in particular less than 1% by mass, very particularly preferably less than 0.2% by mass, of 3-methylbutanal. A process for preparing n-pentanal-rich C5-aldehyde mixtures from mixtures rich in linear C4-olefins is described in DE 102008 002187.3. If a particular isomer composition is desired in the aldolization product, it can be obtained, for example, by means of a distillation step preceding the aldolization. In the distillation, n-valeraldehyde and 2-methylbutanal are separated according to the desired composition. If appropriate, the distillation can be carried out to give a sharper cut and the composition can be obtained by subsequent readdition of one of the components.

As catalyst, it is possible to use hydroxides, hydrogencarbonates, carbonates, carboxylates or mixtures thereof in the form of alkali metal or alkaline earth metal compounds thereof or tertiary amines, in each case as aqueous solutions. Preference is given to using alkali metal hydroxides such as sodium hydroxide as aqueous catalyst solutions.

The concentration of the basic catalyst in the aqueous catalyst solution is generally in the range from 0.1 to 10% by mass, in particular from 0.1 to 3% by mass. Since water is formed in the reaction, the concentration of the catalyst solution in the feed to the reactor is higher than in the output from the reactor. Owing to the Cannizzaro reaction occurring as secondary reaction, alcohols and carboxylic acids are formed from the starting material and to a lesser extent from the product and accumulate in the catalyst phase in the form of their salts. Discharging part of the catalyst solution and replacing it with an equivalent amount of fresh alkali enables the concentration of the carboxylic acid salts in the aqueous catalyst solution to be kept in the range from 5 to 40% by mass.

The proportion of aqueous catalyst solution based on the organic starting phase can vary within wide limits. If a tube reactor is used in the process of the invention, mass ratios of organic phase to catalyst phase of at least 1:2, preferably greater than 1:10, are possible. An analogous situation applies to the use of stirred vessels.

In specific embodiments of the present invention, the concentration of the catalyst solution is controlled by discharge or recirculation measures.

The temperature of the reaction mixture at the reactor outlet is advantageously above the boiling point of the aqueous catalyst solution in the range from 80° C. to 180° C., in particular from 120 to 150° C. When a stirred vessel is used, this corresponds to the temperature of the reaction mixture. In a flow tube or tube reactor operated adiabatically, this temperature is reached only at the end of the reactor.

The pressure in the reaction apparatus is determined by the vapour pressures of the components in the reaction mixture at the prevailing temperatures. The aldol condensation according to the invention is preferably performed at from 0.1 to 2.0 MPa, particularly preferably from 0.2 to 0.5 MPa.

The reaction apparatus for the aldol condensation can be at least one stirred vessel or a cascade of stirred vessels or at least one tube reactor or a flow tube. In each type of reactor, intensive mixing of the two phases can be ensured by means of stirring devices or static mixers.

In the process of the invention, the aldol condensation of the $C_5$-aldehydes is preferably carried out in a tube reactor containing static mixers, as described, for example, in DE 10 2009 001594.9.

The reaction mixture leaving the reactor is separated into the catalyst phase and the organic product phase. The reaction and work-up are preferably carried out as described in DE 199 56 410.

The reaction mixture leaving the reactor is depressurized into a short-path distillation apparatus, preferably to atmospheric pressure. In the case of high-boiling starting materials, depressurization can be carried out into a low vacuum (0.01 to 0.1 MPa).

The short-path distillation can be carried out as a flash distillation, a distillation in a falling film evaporator, a distillation in a thin film evaporator or a distillation in a combined falling film/thin film evaporator. The flash distillation described below is the preferred variant because it is the simplest in terms of technology. The short-path distillation should subject the reaction product to a very low thermal and chemical stress due to the catalyst and is therefore preferably carried out with residence times of not more than one minute. Comparable distillations have residence times of more than 5 minutes. The short-path distillation, in particular the flash distillation, is preferably carried out adiabatically, resulting in the temperature of the bottom product being lower than that of the feed.

The reaction product is separated largely into an overhead product comprising water and $C_5$-aldehydes and a bottom product comprising aldol condensation products, mainly decenals, and aqueous catalyst phase by the short-path distillation.

The overhead product may contain, in addition to the abovementioned mixture of water and starting material, other low boilers (e.g. pentanols) and small amounts of $\alpha,\beta$-unsaturated aldehydes (decenals). The bottom product may contain, in addition to the mixture of decenals and catalyst phase, higher condensation products, products from the Cannizzaro reaction of the starting materials and small amounts of starting materials.

The preferably uncooled bottom product from the short-path distillation can be separated in a settling vessel into an organic phase (product phase) and an aqueous phase, i.e. the aqueous catalyst phase.

The organic product phase is washed with water to remove traces of catalyst, preferably using the aqueous phase of the overhead product of the short-path distillation, and removed from the process. This crude product can be directly used further in the third reaction stage, namely the selective hydrogenation. Optionally, high boilers (higher aldol addition and aldol condensation products) can additionally be separated off and recirculated at least partly to the condensation reactor.

The aqueous catalyst phase is, if appropriate together with washing water obtained, recirculated to the aldol condensation reaction. A small part of the catalyst phase can be discharged and replaced by an equivalent amount of fresh catalyst in order to keep the level of by-products constant.

The overhead product of the short-path distillation is condensed at a temperature which is both below the boiling point of water and below that of a minimum azeotrope. This gives a liquid mixture which can be separated into an organic phase and an aqueous phase.

The organic phase of the overhead product is optionally pumped back into the aldol condensation reactor; a part is discharged if appropriate.

Part of the aqueous lower phase can, for example, be used for washing of the product phase, as has been mentioned above.

The other part of the aqueous phase of the overhead product or the entire aqueous phase serves for discharge of the water of reaction. Organic substituents, especially starting material, are still present in solution in the aqueous phase. The wastewater can be sent to the water treatment plant, either directly or after preliminary purification. The preliminary purification can be carried out by stream stripping or by azeotropically distilling of organic substances.

In the condensation of n-pentanal, 2-propylheptenal is formed as primary aldol condensation product. If 2-methylbutanal is present in the $C_5$-aldehyde, 2-propyl-4-methylhex-2-enal is formed by cross aldol condensation. If 3-methyl-butanal is additionally present in the $C_5$-aldehyde mixture, the following unsaturated aldehydes can be formed as further primary aldol condensation products: 2-isopropyl-5-methylhex-2-enal, isopropyl-4-methylhex-2-enal, 2-propyl-5-methylhex-2-enal and 2-isopropylhept-2-enal. According to the invention, the proportion of 2-propylhept-2-enal based on the sum of all decenals is over 90% by mass.

The crude aldol condensation product, which in addition to the decenals contains mainly higher aldol condensates, can be purified, for example by distillation, before the next stage. Crude decenal mixtures are preferably used in the third stage, viz. the selective hydrogenation.

The selective hydrogenation, in which only the olefinic double bond in decanal is hydrogenated, is carried out using catalysts which can contain palladium, platinum, rhodium and/or nickel as hydrogenation-active component. The metals can be used in pure form, as compounds with oxygen or as alloys. Preferred catalysts are those in which the hydrogenation-active metal has been applied to a support. Suitable support materials are aluminium oxide, magnesium oxide, silicon oxide, titanium dioxide and mixed oxides thereof and also activated carbon. Among these catalysts, particularly preferred catalysts are palladium on activated carbon and palladium on aluminium oxide.

In the case of catalysts comprising palladium and a support, the palladium content is from 0.1 to 5% by mass, preferably from 0.2 to 1% by mass. Particular preference is given to using a catalyst comprising aluminium oxide, preferably γ-aluminium oxide, and having a Pd content of from 0.3 to 0.7% by mass. The catalyst can, if appropriate, contain modifying substances, for example alkali metal components such as sodium compounds in concentrations of up to 3% by mass.

The hydrogenation can be carried out continuously or batchwise and either in the gas phase or the liquid phase. Hydrogenation in the liquid phase is preferred since the gas-phase process requires a higher energy input because of the necessity of circulating large volumes of gas. For the continuous liquid-phase hydrogenation, it is possible to choose a variety of process variants. It can be carried out adiabatically or virtually isothermally, i.e. with a temperature increase of less than 10° C., in one or more stages. In the latter case, the reactors can be operated adiabatically or virtually isothermally or one can be operated adiabatically and the others can be operated virtually isothermally. Furthermore, it is possible to carry out the selective hydrogenation in a single pass or with recirculation of product.

The hydrogenation is carried out in cocurrent in the mixed liquid/gas phase or in the liquid phase in three-phase reactors, with the hydrogen being finely dispersed in a manner known per se in the liquid to be hydrogenated. In the interests of a uniform distribution of liquid, improved removal of heat of reaction and a high space-time yield at a high selectivity, the reactors are preferably operated with high liquid loadings of from 15 to 300 m$^3$, in particular from 25 to 150 m$^3$, per m$^2$ of cross section of the empty reactor an hour. One hydrogenation process for preparing decanals is, for example, liquid-phase hydrogenation in two or more reactors which are all operated with recirculation of product, as described in U.S. Pat. No. 5,831,135.

When palladium catalysts, for example 0.5% by mass on aluminium oxide, are used, the selective hydrogenation of 2-propylheptenal to 2-propylheptanal is preferably carried out at temperatures in the range from 120 to 180° C., in particular from 140 to 160° C., and a pressure of from 1.5 to 5 MPa, in particular from 2 to 3 MPa.

The hydrogenation product comprises decenals together with small amounts of decanols formed by overhydrogenation, small amounts of C$_5$-aldehydes and C5-alcohols and high boilers, mainly higher aldol condensation products and hydrogenation products thereof. The content of 2-propylheptanal based on the decanal fraction is over 85% by mass.

High boilers and/or low boilers can be separated off from the crude hydrogenation product mixture before the next reaction step, viz. the oxidation. A work-up by distillation is preferably omitted.

The oxidation of the decanal mixture to form the corresponding mixture of isomeric carboxylic acids can in principle be carried out in a manner known per se. As oxidant, it is possible to use oxygen, air or other oxygen-containing gas mixtures. The oxidation can be carried out uncatalysed or catalysed. In the latter case, transition metal compounds, in particular cobalt and manganese compounds, are used as catalyst. The oxidation can be carried out at atmospheric pressure or superatmospheric pressure. According to the process of the invention, the oxidation is carried out without catalyst and without further stabilizing additives.

The following examples illustrate the invention.

EXAMPLES

Preparation of 2-propylheptanal (Starting Material for the Aldehyde Oxidation)

A mixture having a high proportion of n-pentanal was firstly prepared from a mixture of linear C4-olefins. n-Pentanal (n-valeraldehyde) and further aliphatic C5-aldehydes also formed were subsequently converted by aldol condensation into the α,β-unsaturated C$_{10}$-aldehydes having a proportion of at least 80% by mass of 2-propylheptenal, based on the total amount of aldol condensation products. 2-Propylheptenal was subsequently converted into the desired product 2-propylheptanal by selective hydrogenation.

Hydroformylation:

A process for preparing n-pentanal-rich C5-aldehyde mixtures from a mixture containing linear C4-olefins is described in DE 10 2008 002187.3, which serves as basis.

Aldolization:

In a continuous experimental plant comprising a tube reactor (20 mm diameter, 4000 mm length) filled with static mixing elements from Sulzer, n-valeraldehyde was converted into 2-propylheptenal at a throughput of 8 l/h in the presence of an aqueous 2% strength sodium hydroxide solution as catalyst (throughput of 80 l/h) at 130° C. and 0.3 MPa. After leaving the reactor, the aqueous catalyst phase was separated from the aldehyde phase in a 5 l separation vessel at 80° C. and conveyed back into the reactor by means of a circulation pump. The organic phase separated off was collected in a 100 l stainless steel vessel.

The crude product output from the n-valeraldehyde aldolization has, according to GC analysis, the following composition in percent by mass: 4.93% of n-valeraldehyde, 0.47% of 2-methylbutanol, 0.30% of pentanol, 0.51% of 2-propyl-4-methylhexenal, 91.81% of 2-propylheptenal and 1.98% of residue.

Selective Hydrogenation:

The output from the aldolization comprising crude 2-propylheptenal was hydrogenated selectively in the liquid phase over the palladium catalyst H 14535 (0.5% of Pd on aluminium oxide), procured from Degussa, at 160° C. and 2.5 MPa in a circulation apparatus to form 2-propylheptanal. For this purpose, 200 ml/h of starting material were passed continuously over 400 ml of catalyst, corresponding to a space velocity over the catalyst of 0.5 h$^{-1}$.

The following typical composition in % by mass of the hydrogenation product was determined by GC: 2.80% of n-valeraldehyde, 0.15% of 2-methylbutanol, 2.14% of n-pentanol, 1.09% of nonane, 0.12% of nonanone, 86.65% of 2-propylheptanal, 0.68% of 2-propylheptenal, 4.27% of 2-propylheptanol and 2.1% of high boilers.

Example 1

Preparation of 2-propylheptanoic Acid/Comparative Example

The preparation of 2-propylheptanoic acid by liquid-phase oxidation of 2-propyl-heptanal was carried out in a heatable 6 l double-walled stirred vessel. The hydrogenation product from the above-described selective hydrogenation containing about 86.7% by mass of 2-propylheptanal was used as starting material.

For a reaction batch, 5050 g of liquid starting material were placed in the reactor. A nitrogen/oxygen mixture was used as reaction gas and was uniformly distributed in the liquid in the lower part of the reactor by means of a frit.

A constant stream of nitrogen of 30 standard l/h and a stream of oxygen regulated according to the consumption by the reaction by means of an on-line measurement of the oxygen content in the offgas were metered into the reactor. A constant stream of nitrogen of 330 standard l/h was metered into the gas space of the reactor in the upper part of the reactor. A maximum oxygen content in the offgas of 6% by volume was permitted. The oxidation of the $C_{10}$-aldehyde mixture was carried out at reaction temperatures of 50 and 70° C. and a reaction pressure of 0.3 MPa. The progress of the oxidation was determined by regular sampling and subsequent GC analysis.

Under the reaction conditions selected, crude products whose composition is listed in Table 1, column 2 and column 3, were obtained after the experiment had run for 4.5 hours.

TABLE 1

Product composition/Comparative Example

| Component | Oxidation at 50° C. percent by mass | Oxidation at 70° C. percent by mass |
|---|---|---|
| n-Valeraldehyde | 0.56 | 0.23 |
| 2-Methylbutanol | 0.17 | 0.12 |
| n-Pentanol | 2.45 | 1.73 |
| Pentyl formate | 0.02 | 0.62 |
| C5-acids | 1.81 | 2.25 |
| Nonane | 1.09 | 9.82 |
| Nonanone | 1.55 | 8.91 |
| C9-alcohols | 8.68 | 18.34 |
| 2-Propylheptanal | 27.32 | 0.26 |
| 2-Propylheptenal | 0.48 | 0.16 |
| C10-alcohols | 5.73 | 5.47 |
| 2-Propylheptanoic acid | 49.79 | 51.62 |
| High boilers | 0.35 | 0.43 |

As can be seen from Table 1, the 2-propylheptanal was virtually completely reacted at a reaction temperature of 70° C. Apart from the desired product of value 2-propylheptanoic acid, a series of by-products such as the $C_9$-paraffin nonane, the $C_9$-ketone nonanone and $C_9$-alcohols were obtained at this temperature. The formation of by-products led to a severe reduction in selectivity. Reducing the reaction temperature to 50° C. enabled the selectivity of 2-propylheptanoic acid formation to be improved, albeit at a significantly lower conversion.

Example 2

Preparation of 2-propylheptanoic Acid/According to the Invention

Using the experimental procedure described in Example 1, 5100 g of starting material containing about 86.6% by mass of 2-propylheptanal were oxidized in the liquid phase at reaction temperatures according to the invention of 25 and 35° C., a reaction pressure of 0.3 MPa and an oxygen content of 6% by volume in the offgas to 2-propylheptanoic acid.

Under the reaction conditions selected, crude products whose composition is listed in Table 2, column 2 and column 3, were obtained after the experiment had run for 6 hours.

TABLE 2

Product composition

| Components | Oxidation at 25° C. Percent by mass | Oxidation at 35° C. Percent by mass |
|---|---|---|
| n-Valeraldehyde | 0.00 | 0.08 |
| 2-Methylbutanol | 0.15 | 0.16 |
| n-Pentanol | 2.10 | 2.21 |
| Pentyl formate | 0.00 | 0.04 |
| C5-acids | 0.00 | 2.43 |
| Nonane | 0.79 | 0.72 |
| Nonanone | 0.35 | 0.89 |
| $C_9$-alcohols | 6.96 | 8.85 |
| 2-Propylheptanal | 7.48 | 3.88 |
| 2-Propylheptenal | 0.61 | 0.57 |
| $C_{10}$-alcohols | 6.34 | 6.21 |
| 2-Propylheptanoic acid | 74.55 | 73.46 |
| High boilers | 0.58 | 0.44 |

As can be seen from Table 2, the selectivity of the 2-propylheptanal oxidation could be significantly improved by reducing the reaction temperatures to 35° C. At a reaction temperature of 25° C. (Table 2, column 2), virtually no $C_9$-paraffins, no $C_5$-acids and no $C_9$-ketone are formed. The selectivity of the formation of acid at this temperature is reduced only by the formation of $C_9$-alcohols. The same behaviour also applies for the oxidation experiment at 35° C. Here too, the selectivity was reduced mainly by the undesirable formation of $C_9$-alcohols.

Example 3

Preparation of 2-propylheptanoic Acid in the Presence of Mn/Cu Catalyst/Comparative Example According to the process of the invention, the oxidation of the $C_{10}$-aldehyde mixture to corresponding $C_{10}$-carboxylic acid is carried out without catalyst. In the following example, the results of the comparative oxidation of 2-propylheptanal in the presence of Cu and Mn salts as catalyst are reported.

For this purpose, 250 ppm of copper and 250 ppm of manganese in the form of acetates were dissolved in 5040 g of starting material containing about 86.6% by weight of 2-propylheptanal before the oxidation. The reaction mixture was then oxidized by the procedure described in Example 1 at 35° C., a reaction pressure of 0.3 MPa and 6% by volume of oxygen in the offgas. For comparative purposes, the oxidation was carried out without catalyst under the same conditions. After the experiment had run for 4 hours, the composition of the product mixture was determined by GC analysis. The composition of the crude products obtained with and without catalyst is shown in Table 3, columns 2 and 3.

TABLE 3

Product composition

| Component | Without catalyst percent by mass | With Cu, Mn catalyst percent by mass |
|---|---|---|
| n-Valeraldehyde | 0.28 | 0.21 |
| 2-Methylbutanol | 0.17 | 0.10 |
| n-Pentanol | 2.38 | 1.95 |
| Pentyl formate | 0.00 | 0.03 |
| C5-acids | 1.89 | 1.67 |
| Nonane | 0.67 | 12.34 |
| Nonanone | 0.72 | 4.43 |
| C9-alcohols | 7.03 | 7.12 |
| 2-Propylheptanal | 24.71 | 10.42 |
| 2-Propylheptenal | 0.46 | 0.18 |

TABLE 3-continued

| | Product composition | |
|---|---|---|
| Component | Without catalyst percent by mass | With Cu, Mn catalyst percent by mass |
| C10-alcohols | 5.59 | 5.85 |
| 2-Propylheptanoic acid | 55.75 | 55.02 |
| High boilers | 0.39 | 0.68 |

As shown in Table 3, the conversion of the 2-propylheptanal oxidation was considerably improved in the presence of a homogeneous copper-manganese catalyst compared to the uncatalysed reaction. The residue contents of 2-propyl-heptanal of about 10.42% by mass determined after 4 hours in the presence of catalyst are lower than the corresponding residue contents of 24.71% by mass of 2-propylheptanal in the uncatalysed oxidation. However, the selectivity of the catalysed oxidation was significantly worse compared to the oxidation without catalyst. As can be seen from Table 3, column 3, the selectivity in the homogeneously catalysed oxidation was reduced by the formation of by-products such as nonane and nonanone. As a result, the yield of isomeric decanecarboxylic acids is comparable to the yield in the uncatalysed oxidation despite higher conversions of about 55% by mass of 2-propylheptanoic acid.

The experiments thus show that an uncatalysed oxidation by means of oxygen at low temperatures is advantageous for preparing 2-propylheptanoic acid in high yield from 2-propylheptanal.

The invention claimed is:

1. A process for preparing a mixture of isomeric decanecarboxylic acids, the process comprising:
   a) hydroformylating a hydrocarbon mixture comprising linear C4-olefins, in the presence of a rhodium-containing catalyst system, to obtain a mixture of aliphatic C5-aldehydes;
   b) condensing, by aldol condensation, the mixture of aliphatic C5-aldehydes, to obtain a mixture of unsaturated C10-aldehydes;
   c) hydrogenating, by selective hydrogenation, the mixture of unsaturated C10-aldehydes, to obtain a mixture of aliphatic C10-aldehydes;
   d) oxidizing, by uncatalysed oxidation, the mixture of aliphatic C10-aldehydes to obtain a mixture of isomeric decanecarboxylic acids, said mixture of acids comprising at least 70% by mass of 2-propylheptanoic acid, based on a total content of isomeric decanecarboxylic acids.

2. The process of claim 1, wherein the hydrocarbon mixture comprises up to 5% by mass of isobutene, based on a fraction of the linear C4-olefins.

3. The process of claim 1, wherein the oxidizing d) is carried out in a temperature range from 25 to 35° C.

4. The process of claim 1, wherein the oxidizing d) is carried out at a pressure in the range from 0.1 to 1 MPa.

5. The process of claim 1, wherein the oxidizing d) is carried out at a pressure in the range from 0.1 to 0.5 MPa.

6. The process of claim 2, wherein the oxidizing d) is carried out in a temperature range from 25 to 35° C.

7. The process of claim 2, wherein the oxidizing d) is carried out at a pressure in the range from 0.1 to 1 MPa.

8. The process of claim 3, wherein the oxidizing d) is carried out at a pressure in the range from 0.1 to 1 MPa.

9. The process of claim 2, wherein the oxidizing d) is carried out at pressure in the range from 0.1 to 0.5 MPa.

10. The process of claim 3, wherein the oxidizing n d) is carried out at pressure in the range from 0.1 to 0.5 MPa.

11. The process of claim 4, wherein the oxidizing d) is carried out at pressure in the range from 0.1 to 0.5 MPa.

* * * * *

UNITED STATES PATENT AND TRADEMARK OFFICE
CERTIFICATE OF CORRECTION

PATENT NO.         : 8,907,129 B2                                                   Page 1 of 1
APPLICATION NO.    : 13/386523
DATED              : December 9, 2014
INVENTOR(S)        : Michael Grass et al.

It is certified that error appears in the above-identified patent and that said Letters Patent is hereby corrected as shown below:

On the title page, Item (30), the Foreign Application Priority Data Information has been omitted.
Item (30) should read:

--(30)             Foreign Application Priority Data

Jul. 23, 2009         (DE)....................102009027978.4--

Signed and Sealed this
Thirty-first Day of March, 2015

Michelle K. Lee
*Director of the United States Patent and Trademark Office*